(12) United States Patent
Bachlechner et al.

(10) Patent No.: US 10,847,396 B2
(45) Date of Patent: Nov. 24, 2020

(54) FOUP MEASUREMENT CHAMBER

(71) Applicant: Fabmatics GmbH, Dresden (DE)

(72) Inventors: Martin Bachlechner, Dresden (DE);
Nadja Erler-Lohse, Dresden (DE);
Cornelius Günther, Dresden (DE)

(73) Assignee: Fabmatics GmbH, Dresden (DE)

( * ) Notice: Subject to any disclaimer, the term of this patent is extended or adjusted under 35 U.S.C. 154(b) by 81 days.

(21) Appl. No.: 16/091,532

(22) PCT Filed: Apr. 4, 2017

(86) PCT No.: PCT/EP2017/057917
§ 371 (c)(1),
(2) Date: Oct. 5, 2018

(87) PCT Pub. No.: WO2017/174540
PCT Pub. Date: Oct. 12, 2017

(65) Prior Publication Data
US 2019/0131155 A1 May 2, 2019

(30) Foreign Application Priority Data
Apr. 5, 2016 (DE) .......... 10 2016 205 597

(51) Int. Cl.
*F16K 31/02* (2006.01)
*H01L 21/673* (2006.01)
*G05D 7/06* (2006.01)
*G01F 1/34* (2006.01)
*G01N 33/00* (2006.01)

(52) U.S. Cl.
CPC ..... *H01L 21/67389* (2013.01); *G05D 7/0635* (2013.01); *H01L 21/67393* (2013.01); *G01F 1/34* (2013.01); *G01N 33/0036* (2013.01)

(58) Field of Classification Search
CPC ........ H01L 21/67389; H01L 21/67393; G05D 7/0635; G01F 1/34; G01N 33/0036
USPC ........ 137/487.5, 552, 554, 557; 73/714, 723
See application file for complete search history.

(56) References Cited

U.S. PATENT DOCUMENTS

| | | | |
|---|---|---|---|
| 6,123,120 A * | 9/2000 | Yotsumoto | H01L 21/67769 141/59 |
| 9,305,817 B2 * | 4/2016 | Kaise | H01L 21/67772 |
| 10,332,766 B2 * | 6/2019 | Sasaki | H01L 21/67389 |
| 10,438,829 B2 * | 10/2019 | Murata | H01L 21/67769 |
| 2001/0042439 A1 | 11/2001 | Roberson et al. | |

(Continued)

FOREIGN PATENT DOCUMENTS

DE 102013222900 A1 5/2015
EP 1059660 A2 12/2000
(Continued)

Primary Examiner — Minh Q Le
(74) Attorney, Agent, or Firm — Michael Soderman (57) ABSTRACT

A purge measuring system for front opening unified pods ("FOUPs") which are positioned in a FOUP nest. Along with at least one unoccupied/occupied sensor for the FOUP nest, at least one gas feed line and one gas discharge line for feeding and discharging flushing gas respectively is provided. At least one pressure sensor, a flowmeter and a regulator valve are arranged in each gas feed line. The valve is regulated based on the measuring results of pressure sensor and flowmeter. At least one moisture sensor and/or one oxygen sensor are arranged in each gas discharge line.

11 Claims, 4 Drawing Sheets

(56) References Cited

U.S. PATENT DOCUMENTS

| | | |
|---|---|---|
| 2005/0087299 A1 | 4/2005 | Okabe et al. |
| 2006/0288664 A1* | 12/2006 | Okabe ............... H01L 21/67393 |
| | | 53/510 |
| 2008/0177414 A1 | 7/2008 | Harel et al. |
| 2009/0053017 A1 | 2/2009 | Shmuelov |
| 2012/0096740 A1* | 4/2012 | Naylor ..................... F17D 1/04 |
| | | 34/562 |
| 2014/0000757 A1* | 1/2014 | Takahara .......... H01L 21/67769 |
| | | 141/8 |
| 2015/0170939 A1 | 6/2015 | Rebstock |
| 2015/0235884 A1* | 8/2015 | Jang .................. H01L 21/67389 |
| | | 414/279 |
| 2015/0380288 A1 | 12/2015 | Hirano |
| 2016/0358799 A1* | 12/2016 | Murata .............. H01L 21/67389 |
| 2017/0025297 A1* | 1/2017 | Kudo ................ H01L 21/67772 |
| 2017/0062243 A1* | 3/2017 | Omori ............... H01L 21/67769 |
| 2017/0069516 A1* | 3/2017 | Chen ........................ B05B 9/01 |
| 2017/0221743 A1* | 8/2017 | Kondoh ............ H01L 21/67775 |
| 2018/0012779 A1* | 1/2018 | Oh ........................ H01L 21/673 |
| 2018/0244470 A1* | 8/2018 | Murata ............. H01L 21/67769 |
| 2018/0247846 A1* | 8/2018 | Murata ............. H01L 21/67769 |
| 2018/0374733 A1* | 12/2018 | Pannese ........... H01L 21/67772 |
| 2019/0035660 A1* | 1/2019 | Lin ................... H01L 21/67775 |

FOREIGN PATENT DOCUMENTS

| | | | |
|---|---|---|---|
| EP | 2128890 | A2 | 12/2009 |
| EP | 2453310 | A2 | 5/2012 |

* cited by examiner

FOUP MEASUREMENT CHAMBER

CROSS REFERENCE TO RELATED APPLICATIONS

This application is the U.S. national stage of International Application No. PCT/EP2017/057917, filed on 2017 Apr. 4. The international application claims the priority of DE 102016205597.6 filed on 2016 Apr. 5; all applications are incorporated by reference herein in their entirety.

BACKGROUND

The present invention has as its subject matter a purge measuring system for FOUPs which permits the processes taking place in the FOUPs to be monitored, controlled, regulated and documented even during the purging operations.

With complex components, the production of semiconductor chips can possibly take several months. During this product cycle time, the wafers are processed in a multiplicity of tools. The cycle time is not only made up of the process and transport times but also of the times between the treatment steps, in which the wafers have to wait for the next treatment step.

The wafer treatment (processing) must be documented in detail during the whole cycle in order to be able to fulfil the quality assurance requirements. As well as the actual treatment of the wafers, the conditions under which the wafers are stored between individual treatment steps are therefore also of central importance. Depending on the environmental conditions, chemical and physical changes, particularly at the wafer surface, also take place in the quiescent state. This leads to the storage conditions also having to be defined and monitored.

A range of technical solutions for fulfilling these varied and sometimes diverging requirements is known for this purpose.

In modern fabrication plants for producing semiconductors (chip production), the wafers are consolidated into units (batches—usually 25 wafers) and moved in transport containers. However, while in older semiconductor fabrication plants (fabs) these containers were often transported manually and the containers were simple plastic housings with slide-in compartments for the wafers, these designs no longer meet current requirements. According to the prior art, the wafers are therefore transported and stored in FOUPs (Front Opening Unified Pod). These FOUPs likewise contain inserts for receiving the wafers. However, a FOUP can also be transported by machine. Opening and closing of the front door as well as the removal and insertion of wafers also take place automatically.

Fully automated production lines, in which the FOUPs are automatically transported from one tool to the next or from a tool to a buffer store or from said buffer store to a further tool, are realised using FOUPs. Defined storage conditions, which, in particular, prevent storage durations of different lengths leading to different surface properties of the wafers, must be created in the buffer store. It has therefore been shown to be advantageous to flush the surfaces of the wafers with inert gases in order to displace residues of oxygen from the FOUPs and thus prevent, or at least severely limit, oxidation and diffusion processes. Inert gases, preferably argon or nitrogen, are used as suitable flushing gases. XCDA (Extreme Clean Dry Air), for example from the company Entegris, is also used as a flushing gas for areas of application which do not need to be oxygen-free. XCDA is used particularly in clean rooms of limited size, as here an increase in the concentration of inert gases could lead to a displacement of oxygen, as a result of which working safety could no longer be guaranteed. The holding positions of the FOUPs in buffer stores, which are usually attached to the clean room ceiling, are called FOUP nests. In the following, FOUP nests are understood to mean all FOUP holding positions which are used for the interim storage or flushing of the wafers with flushing gases without being part of a tool. FOUP nests therefore do not necessarily have to be suspended from the clean room ceiling.

The FOUPs are transported by means of their own transport devices. The FOUPs are unloaded in the tool loading ports, the wafers fed to the treatment process and then reloaded into the FOUPs. The wafers are not processed in the FOUP nests of the buffer store or buffer stores but merely flushed with inert gas. This flushing is referred to as purging. The buffer stores are frequently formed as FOUP nests on struts suspended from the clean room ceiling. When depositing the FOUPs in the nests, they are placed on base plates which have guide pins (kinematic coupling pin) and gas connectors. These gas connectors engage in an interlocking manner in corresponding mating pieces in the FOUP bases forming a seal. The gas feed is enabled in this way. The gas feed system can likewise be installed overhead or, as clean room floors are usually perforated double floors, at floor level, in the intermediate space between the perforated floor and the clean room subfloor.

The design of the FOUPs, their base plates and the FOUP nests vary depending on the manufacturer.

The tools of the semiconductor industry in the clean rooms are frequently replaced due to advancing technical development. Newly installed tools sometimes come with their own FOUP nests, the positions of the base plate connectors of which do not correspond to those of those previously used.

In order to match the FOUP nests to the FOUPs used in the production process, in US 2014/0360531 A1 the use of an adapter is proposed. This adapter must be replaceable. It has two gas ports which serve to feed in and discharge the flushing gas. A valve on the feed gas port can control the gas flow. The gas is discharged by means of a discharge valve which receives the gas leaving the FOUP. The adapter therefore merely transposes the connectors of the FOUP nest to the differently positioned FOUP connectors and, by means of the valves, releases the gas feed and discharge as soon as a FOUP is detected on the adapter. No further information relating to the conditions and processes in the FOUP is recorded.

DE 10 2013 222 900 A1 describes a flexible Purge Management System, which is capable of controlling and regulating the flushing processes in a plurality of FOUPs independently of one another by means of a multi-layer controller structure. In particular, the gas feed and the monitoring of the gas flow are described. Furthermore, it is provided that the FOUP nests be matched to different FOUP designs by means of replaceable adapter plates. The gas emerging from the FOUPs is optionally released into the clean room without further measures. This is possible, as the gases are inert gases. The actual conditions in the FOUPs are also not recorded with this solution.

A purge system for standard pods (the function of which corresponds to the FOUPs) is described in US 2001/0 042 439 A1. Here, a series of sensors is provided in the gas feed to the FOUP. Furthermore, it is proposed that sensors for moisture, oxygen and particles also be arranged in the gas flow extracted from the FOUP. A bypass for the gas feed from the feed line directly to the sensors of the outlet line is also provided. The system is permanently installed in the respective FOUP nest or in a system for flushing a plurality of FOUPs.

SUMMARY

The subject matter of the present invention is a purge measuring system for FOUPs which are positioned in a FOUP nest. Along with at least one unoccupied/occupied sensor for the FOUP nest, at least one gas feed line and one gas discharge line for feeding and discharging flushing gas respectively is provided. At least one pressure sensor, a flowmeter and a regulator valve are arranged in each gas feed line. The valve is regulated based on the measuring results of pressure sensor and flowmeter. At least one moisture sensor and/or one oxygen sensor are arranged in each gas discharge line.

DETAILED DESCRIPTION

The object is therefore to also monitor, control, regulate and document the processes taking place in the FOUPs during the purge operations. As a partial objective, it must be provided that existing systems can be retrofitted with the advanced purge solution according to the invention.

According to the invention, the object is achieved by means of a purge measuring system according to claim 1. Advantageous embodiments are disclosed in the referenced sub-claims.

The purge measuring system according to the invention has
At least one unoccupied/occupied sensor for the FOUP nest,
A controllable valve in the gas feed line (as an option, a plurality of controllable valves is possible when a plurality of gas feed lines is present),
At least one gas pressure sensor in each gas feed line,
At least one sensor for moisture or oxygen content in the gas discharge line.

The unoccupied/occupied sensor for the FOUP nest detects whether a FOUP has been placed in the FOUP nest. The detection preferably takes place mechanically (pressure switch) or by means of an RFID read chip. Other measuring methods, such as barcode readers etc., are known from the prior art.

A technical solution according to the prior art is chosen for the controllable valve. As selection criteria, along with the suitability of the clean room, the quantity of gas to be throughput, further typical valve design criteria and the electrical supply data must be taken into account. Viewed in the direction of flow, the controllable valve is connected upstream of at least one pressure sensor (which is used to determine a pressure difference with respect to the gas discharge line).

Like all other components, the gas pressure sensors must be suitable for use in a clean room and their measuring ranges correspond to the expected pressures. The person skilled in the art chooses appropriate sensors from the commercially available range according to the prior art.

The sensors for moisture or oxygen content are also chosen by the person skilled in the art from the commercially available range according to the prior art.

As an option, gas flow sensors, pressure monitoring switches in the purge gas feed line in the form of limit switches for over and under pressure, as well as particle filters before each gas inlet are provided in a FOUP. The particle filters are preferably arranged in the FOUP immediately before the gas inlet so that no further sensors (only the pipework of the gas feed line) are arranged between particle filter and gas inlet. Furthermore, as an option, it is also possible to arrange further sensors (preferably moisture and oxygen sensors) in the feed line. Particularly preferably, optional sensors of this kind correspond to similar sensors (measuring the same measured quantity) in the gas discharge line. Advantageously, this enables differential measurements between gas feed and discharge.

Furthermore, both a moisture and an oxygen sensor are optionally arranged in the gas discharge line. As an option, a particle sensor is arranged in the gas discharge line. The particle sensor is preferably arranged immediately after the gas outlet of the FOUP so that no further sensors are present between particle sensor and gas outlet. In a particularly preferred embodiment, a pressure sensor, which is preferably designed as a differential pressure sensor between gas feed and gas discharge, is provided. The differential pressure sensor then replaces the gas pressure sensor. Optionally, the differential pressure between gas feed and discharge can also be determined by calculation (preferably by means of a data-processing device) from the measured values of separate sensors in the gas feed and discharge lines. Preferably, the differential pressure information is used to actuate the controllable valve. Particularly preferably, a flow sensor (flowmeter with analogue output), which measures the gas volume fed to the FOUP, is inserted in the gas feed line. Furthermore, as an option, temperature sensors are provided in the gas feed and/or discharged line. After the gas has passed through the sensors in the gas discharge line, it is preferably released into the clean room. Alternatively, it can be transferred to a gas collection system if appropriate connector options exist.

The sensors can make one-off individual measurements as well as individual measurements at specified time intervals or in accordance with measurement regimes. A continuous measurement can also be carried out (depending on sensor type). In this way, it is possible, in particular, to keep the differential pressure between gas feed and discharge constant during purging and thus guarantee a uniform gas flow through the FOUP. In the preferred embodiment with flowmeter, this is also possible using the measured values of this sensor, so that the use of a pressure sensor in the gas discharge line can possibly be dispensed with.

In a preferred embodiment, the sensors and other components for implementing the measuring system according to the invention are arranged on the underside or beneath an adapter plate for FOUP nests. This adapter plate can be fitted releasably or non-releasably in a FOUP nest and here realise the transposition of the existing gas feed and discharge of the FOUP nest to the gas feed and discharge of the FOUP. In particular, such an adapter plate is integrated into the gas feed and, if necessary, discharge system of a purge management system. Particularly preferably, the sensors and, optionally, a data-processing device, are arranged on the adapter plate (preferably the underside thereof).

The data recorded by the measuring system according to the invention can also be transmitted to an existing data-processing system by cable or wirelessly. The connection is made, for example, by means of the procedure described in DE 10 2013 222 900 A1. Energy is likewise supplied using methods from the prior art (e.g. using cables and connection via plug-in connectors). Optionally, data connection and energy supply can be fed via the same cable. The use of a CAN bus network for data transmission is particularly preferred.

In a preferred embodiment, a local data-processing device is provided, which conditions the sensor data and detects control tasks (e.g. for the regulator valves for maintaining a specified differential pressure). As an option, sensor measurements and/or calculation results of the data-processing device can be buffered. Furthermore, communication with a central or other superimposed data-processing device can be transmitted to this local data-processing device. Programme changes and specified parameters can then also be transmitted from superimposed data-processing devices. In particular, the local data-processing device can undertake tasks of the purge nest controller or the purge bay controller as defined by DE 10 2013 222 900 A1.

The purge measuring system according to the invention enables measured data to be obtained from the gas flow which emerges from the FOUP. Advantageously, this enables conclusions to be drawn relating to the conditions in the FOUP. The measuring frequency can be adapted to the magnitude of the change in the measuring results so that, at the beginning of gas flushing, measurements are made more frequently than when stable flow conditions, which do not have to be monitored so frequently, have been established through the FOUP.

In particular, an optional oxygen sensor in the gas discharge line enables conclusions to be drawn relating to the sealing of the FOUP. When the FOUP has been placed in the FOUP nest and the gas flushing has begun, the air in the FOUP is expelled by the flushing gas (preferably nitrogen or argon). The further progression of the oxygen content in the FOUP enables conclusions to be drawn relating to both the sealing of the FOUP and to oxygen-emitting processes.

An optional moisture sensor enables the water vapour content of the gas emerging from the FOUP to be measured. Advantageously, this enables the quality of previous drying processes to be assessed. In a particularly preferred embodiment, the oxygen sensor and/or the moisture sensor (both or one of the sensors) are arranged in their own common measuring chamber, through which gas emerging from the FOUP flows. The common measuring chamber has a gas feed line, via which the gas emerging from the FOUP is fed, and a gas discharge line, via which the gas leaves the measuring chamber and, if necessary, is fed to further sensors or into the clean room. The common measuring chamber is designed such that the gas passing through the measuring chamber flows around the sensor or sensors. This is achieved, for example, by flow guiding devices, a particularly narrow measuring chamber which leaves no gas paths free other than via the sensors, or other measures of forced guidance. Particularly preferably, there exists a bypass connection with associated valves, which enables flushing gas to be fed into the measuring chamber without this having to pass through the FOUP. This enables the common measuring chamber to be flushed and, if necessary, sensor calibration to be carried out. In addition, moisture precipitation or similar deposits which have emerged from the FOUP are reliably removed. Particularly preferably, the common measuring chamber is flushed when there are no FOUPs in the FOUP nest. The flushing process of the common measuring chamber is controlled by controlled actuation of the appropriate valves, preferably likewise by the data-processing device.

If an optional particle sensor is present in the gas line, contamination on the wafers can be detected. This is detectable from a large particle content in the exhaust air which reduces with time. In particular, it can be detected when the wafers in a tool become contaminated. A comparison of the particle contents in the exhaust air of the purge step before the tool and the purge step after the tool can provide information in this regard.

Preferably, the sensor measurements and the control and regulation variables derived therefrom are stored or fed to a documentation system in some other manner.

DETAILED DESCRIPTION OF THE PREFERRED EMBODIMENTS

Figure 1:
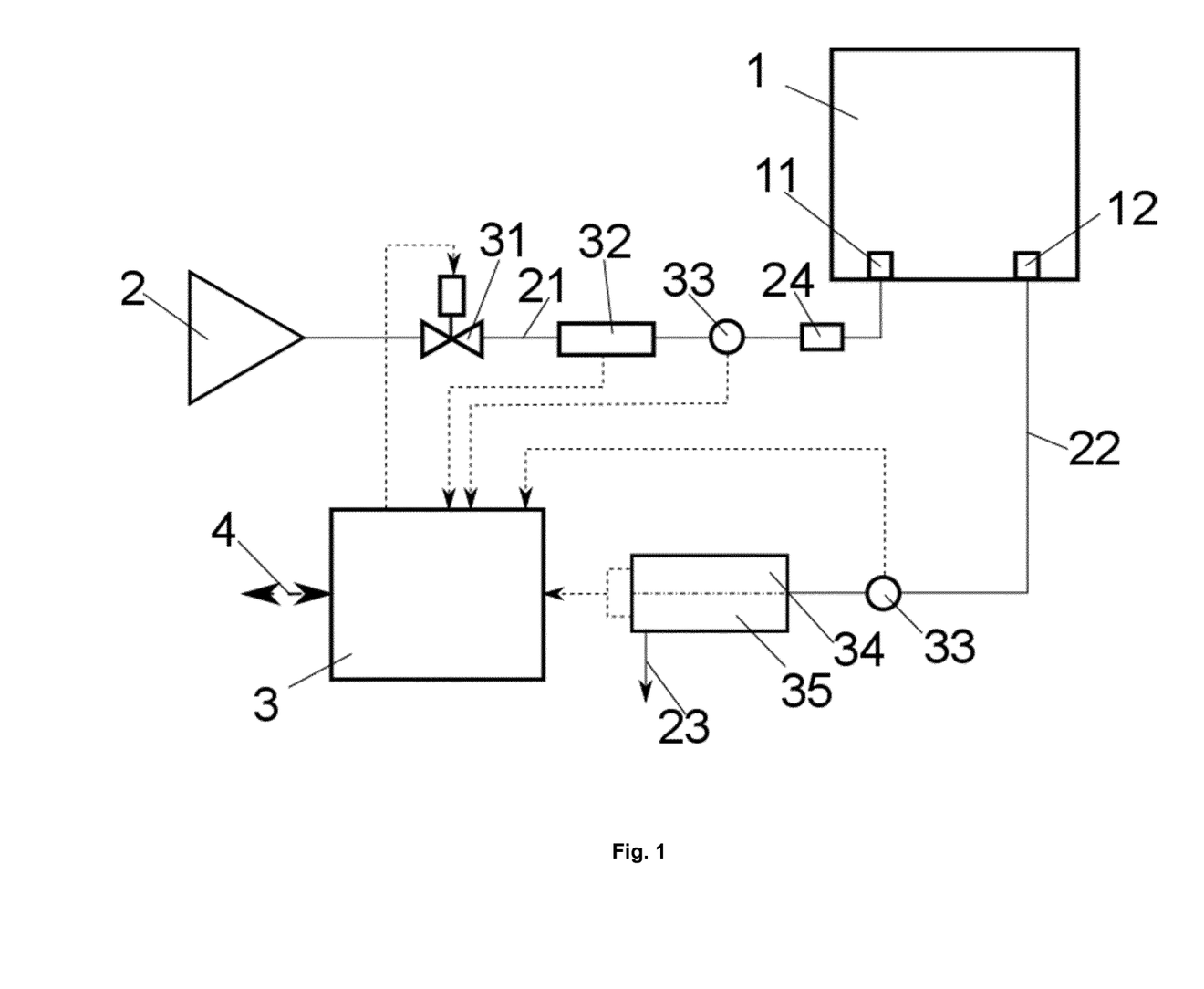
FIG. 1 shows schematically a preferred simple embodiment of the purge measuring system according to the invention.

FIG. 1 shows schematically a preferred simple embodiment of the purge measuring system according to the invention. The purge gas (nitrogen) enters the feed line to the FOUP 1 via the nitrogen supply 2. In doing so, it passes through the regulator valve 31, the flowmeter 32 and the pressure gauge 33. Particles that are carried along are removed from the flushing gas by means of the particle filter 24. The purge gas passes into the FOUP 1 via the nitrogen inlet 11 and leaves it once more via the nitrogen outlet 12. A pressure sensor 33 as well as a moisture sensor 34 and oxygen sensor 35 are arranged in the nitrogen discharge line 22. The nitrogen then leaves the system via the nitrogen outlet 35. The sensor measurements are fed to the data-processing device 3. This calculates the differential pressure between nitrogen feed line 21 and nitrogen discharge line 22 from the measurements of the pressure sensors 33 and generates control signals for the regulator valve 31. In addition, the measured values and the control values and difference values derived therefrom are transmitted via the CAN BUS 4. Reference values for the differential pressure and other values as well as further control data are also transmitted via the CAN bus 4. The unoccupied/occupied sensor, which provides information relating to the occupation state of the FOUP nest, is not shown.

Figure 2:
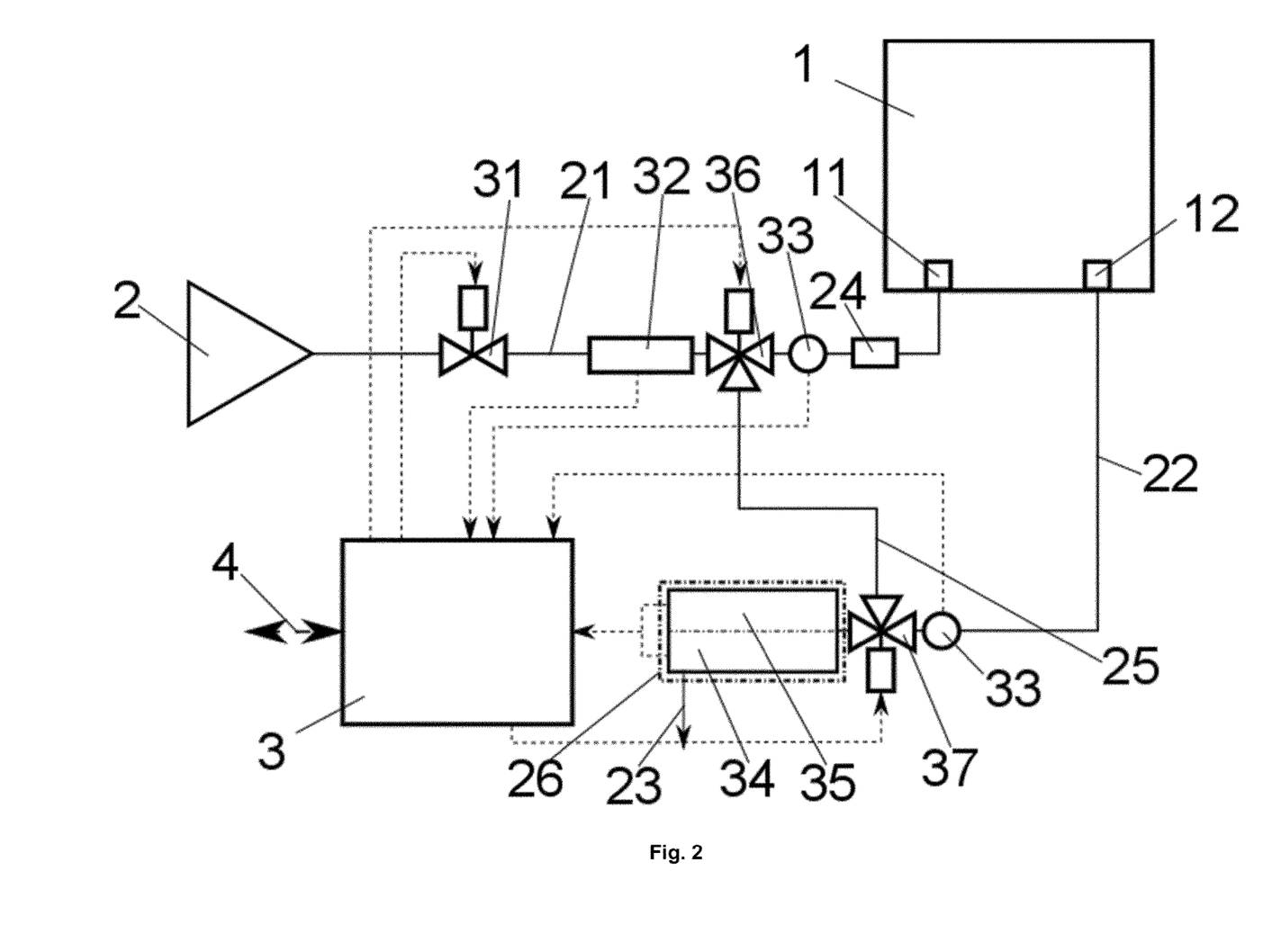
FIG. 2 shows the device according to the invention in the preferred embodiment with a common measuring chamber 26 for moisture and oxygen sensors 34, 35.

FIG. 2 shows the device according to the invention in the preferred embodiment with a common measuring chamber 26 for moisture and oxygen sensors 34, 35. The common measuring chamber 26 can be supplied with flushing gas via the bypass line 25. For this purpose, the two three-way valves 36 and 37 are set so that the gas path to the FOUP nest is closed and to the common measuring chamber 26 is open. The control of the two three-way valves 36, 37 is carried out by the data-processing device 3.

Figure 3:
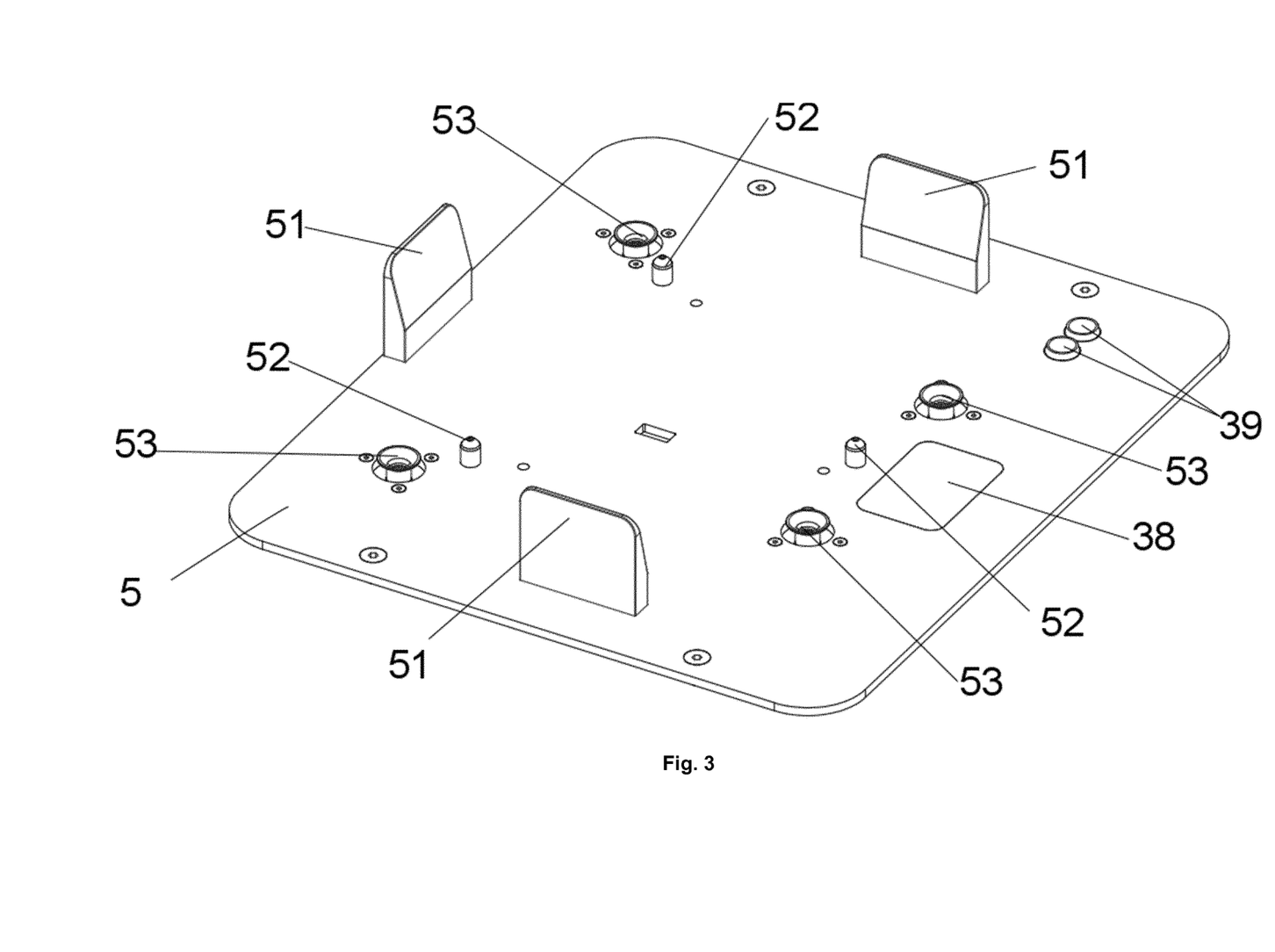
FIG. 3 shows schematically the upper part 5 of an adapter plate, on which a FOUP is placed.

FIG. 3 shows schematically the upper part 5 of an adapter plate, on which a FOUP is placed. The insertion aids 51 ensure that the FOUP is safely positioned over the guide pins 52 of the adapter plate when it is fitted. After lowering, the guide pins 52, which engage in corresponding openings of the underside of the FOUP, prevent unintended movement. In addition, the guide pins 52 guarantee that the corresponding gas connectors 53 of adapter plate and FOUP rest on one another to form a seal. The state of the adapter plate and the electronics arranged thereunder can be monitored by means of the status LEDs 39. The RFID identification chip of a fitted FOUP can be read out through the cover 38 of the RFID antenna. Here, the cover preferably consists of plastic material so that, in contrast to the rest of the top cover 5 of the adapter plate, which is made of metal, it is transparent for the radio waves of the RFID chip. The electronics and the measuring chamber are arranged on a bottom part (not shown) below the top part 5 of the adapter plate. The top part 5 and the bottom part are connected to one another by a housing edge (not shown). The height of the adapter plate is approx. 3 cm.

Figure 4:
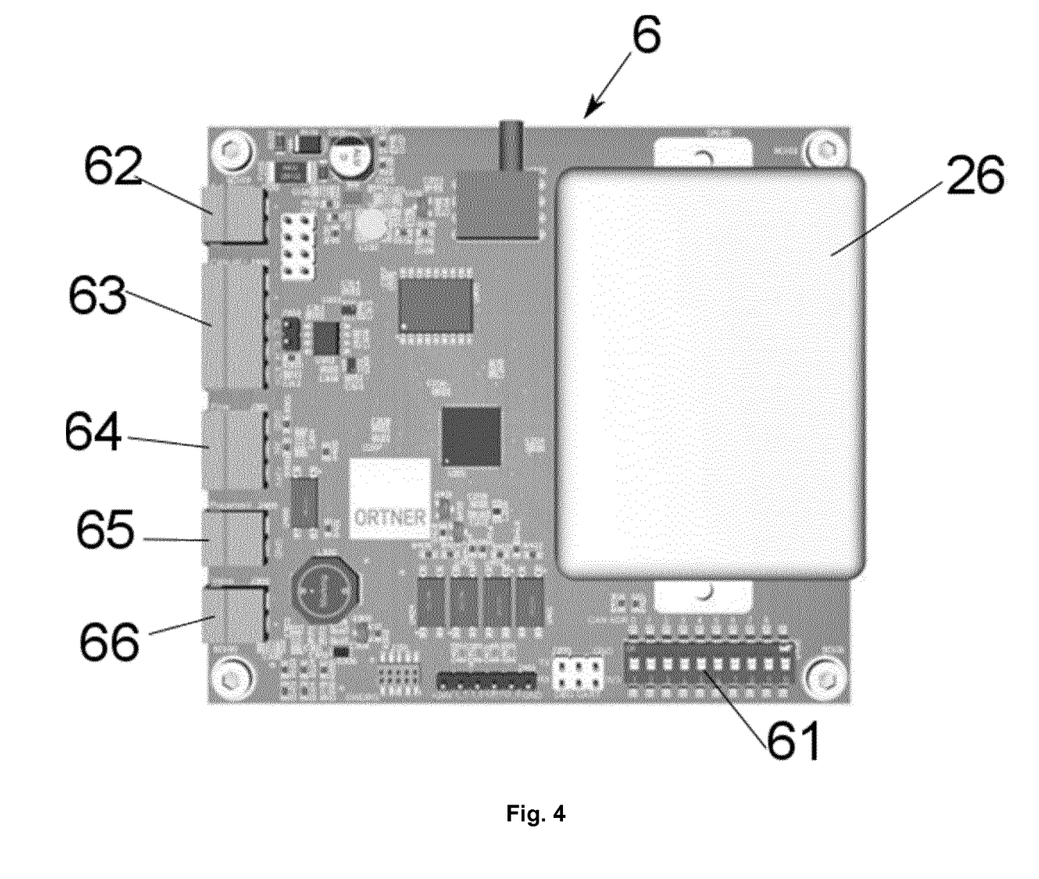
FIG. 4 shows by way of example a board 6 which is arranged below the top part of the adapter plate in the interior thereof.

FIG. 4 shows by way of example a board 6 which is arranged below the top part of the adapter plate in the interior thereof. The connectors for energy supply 62, the CAN BUS interface 63, the flowmeter interface 64, the unoccupied/occupied sensor 65 and the valve control 66 are shown schematically on the left-hand side of the board. A moisture sensor and an oxygen sensor (neither of which are shown) are arranged in the FOUP measuring chamber 26. The CAN BUS address 61 serves to set up the address of the board 6 within the CAN BUS network. Advantageously, a low structure and replacability of the whole assembly is achieved by the direct integration of the measuring chamber 26 on the board 6.

Exemplary Embodiment

A preferred exemplary embodiment according to FIG. 1 is designed with the following components:

The nitrogen supply (nominal diameter 12 mm) 2 supplies up to 99.95% pure nitrogen into the nitrogen feed line 21 as a flushing gas. However, the device described is also suitable for use of XCDA. The regulator valve 31 controls the gas flow in the nitrogen feed line 21. The gas flow is measured with the flowmeter 32. The pressure is measured by means of the pressure sensor 33. After the pressure sensor 33, the nitrogen passes through the particle filter 24. The flushing gas enters the FOUP 1 via the gas inlet 11 and leaves it via the gas outlet 12. The nitrogen discharge line 22 feeds the nitrogen to the pressure sensor 33. From here, the nitrogen passes to the oxygen sensor 34 and to the moisture sensor 35. The measured values of all sensors are brought together in the data processing unit (embedded controller). The data processing unit is connected via an RJ45 connector to an Ethernet, which transports data and calculation results to a central data-processing device and accepts control commands and programmes therefrom. The connection is implemented as a CAN bus. The flow which is to be realised through the FOUP is specified (stored in the programme or manual entry). The data-processing device controls the regulator valve 31 until the flowmeter determines the specified value. In conjunction with the measured value of the pressure sensor 33 arranged at the gas inlet and the measured value of the flowmeter, conclusions can be drawn relating to the sealing of the FOUP (leakage detection).

LIST OF REFERENCE NUMERALS

1 FOUP
11 Gas inlet to FOUP
12 Gas outlet from FOUP
2 Flushing gas supply
21 Flushing gas feed line
22 Flushing gas discharge line
23 Flushing gas outlet
24 Particle filter
25 Bypass line for flushing the common measuring chamber
26 Common measuring chamber
3 Data-processing device
31 Regulator valve
32 Flowmeter
33 Pressure gauge
34 Moisture sensor
35 Oxygen sensor
36 Three-way valve
37 Three-way valve
38 Cover for RFID antenna
39 Status LEDs
4 CAN bus connection
5 Top cover for adapter plate
51 FOUP adapter plate insertion aids
52 FOUP adapter plate guide pins
53 Gas feed and discharge adapter to and from FOUP
6 Control board with common measuring chamber
61 CAN bus addressing
62 Power supply
63 CAN bus interface
64 Flowmeter interface
65 Connector for unoccupied/occupied sensor
66 Valve control

The invention claimed is:

1. Purge measuring system for FOUPs (1) in a FOUP nest having:
   a. At least one unoccupied/occupied sensor for the FOUP nest
   b. at least one gas feed line (21) for feeding flushing gas to the gas inlet (11) of a FOUP (1),
   c. at least one gas discharge line (22) for discharging flashing gas from the gas outlet (12) of a FOUP (1)
   wherein
   at least one pressure sensor (33) is arranged in each gas feed line (21), and
   at least one flowmeter (32) is arranged in each gas feed line (21), and
   a regulator valve (31) is connected upstream of the flowmeter (32) and the pressure sensor (33) in the direction of flow in each gas feed line (21), and
   at least one moisture sensor (34) and one oxygen sensor (35) are arranged in each gas discharge line (22), the at least one moisture sensor (34) and one oxygen sensor (35) are arranged in a measuring chamber (26) which has a chamber gas feed line and a chamber gas discharge line and is designed such that the gas passing through the measuring chamber (26) flows around the sensors, and
   the components of the purge measuring system are arranged on an adapter plate which is releasably or permanently arranged in the FOUP nest, wherein the adapter plate matches the gas connectors of the FOUP nest in position and size to the FOUP (1).

2. Purge measuring system according to claim 1, characterized in that a particle filter (24) is arranged in the gas feed line (21).

3. Purge measuring system according to claim 2, characterized in that no further sensors are arranged between particle filter (24) and gas inlet (11) in the FOUP (1).

4. Purge measuring system according to claim 1, characterized in that a particle sensor is connected in the gas discharge line (22) immediately after the gas outlet (12) of the FOUP (1) viewed in the direction of flow.

5. Purge measuring system according to claim 1, characterized in that the purge measuring system has a local data-processing device (3) to which the sensor measurements are fed.

6. Purge measuring system according to claim 1, characterized in that a pressure sensor (33) is arranged in the gas discharge line (22).

7. Purge measuring system according to claim 6, characterized in that the pressure sensor (33) is arranged immediately after the outlet (12) of the gas from the FOUP (1) and before all further sensors in the gas discharge line.

8. Purge measuring system according to claim 6, characterized in that the pressure sensors (33) in the gas feed line (21) and the gas discharge line (22) are designed as a common differential pressure sensor, or that the local data-processing device (3) calculates the differential pressure from the measurements of the pressure sensors (33) in the gas feed line (21) and the gas discharge line (22).

9. Purge measuring system according to claim 8, characterized in that the local data-processing device (3) controls the regulator valve (31) based on the differential pressure.

10. Purge measuring system according to claim 1, characterized in that the measuring chamber (26) is supplied with flushing gas from the gas feed line (21) via a bypass connection (25) and thereby flushed.

11. Purge measuring system according to claim 5, characterized in that the local data-processing device (3) is connected to a bus system, preferably a CAN bus, via a data connection and feeds measurements from the sensors and/or calculated values to a superimposed data-processing device and/or receives programs, commands and parameters for controlling the purge measuring system from the superimposed data-processing device.

* * * * *